(12) United States Patent
Kadlec et al.

(10) Patent No.: US 7,285,255 B2
(45) Date of Patent: Oct. 23, 2007

(54) DEODORIZING AND SANITIZING EMPLOYING A WICKING DEVICE

(75) Inventors: Leonard Kadlec, Woodbury, MN (US); Daniel Tallman, Roseville, MN (US); Patrick Kilawee, Hugo, MN (US)

(73) Assignee: Ecolab Inc., St. Paul, MN (US)

( * ) Notice: Subject to any disclaimer, the term of this patent is extended or adjusted under 35 U.S.C. 154(b) by 725 days.

(21) Appl. No.: 10/316,513

(22) Filed: Dec. 10, 2002

(65) Prior Publication Data

US 2004/0109799 A1 Jun. 10, 2004

(51) Int. Cl.
*A61L 2/16* (2006.01)
(52) U.S. Cl. .......................... 422/305; 422/37; 210/753
(58) Field of Classification Search ................ 422/37, 422/305; 210/753; 239/34, 44
See application file for complete search history.

(56) References Cited

U.S. PATENT DOCUMENTS

| | | | |
|---|---|---|---|
| 2,424,174 A * | 7/1947 | Jensen et al. ................ 4/225.1 |
| 3,334,789 A | 8/1967 | Kat et al. | |
| 4,258,056 A | 3/1981 | Lentsch ........................ 424/303 |
| 4,284,653 A | 8/1981 | Shigeoka et al. ............ 426/312 |
| 4,295,932 A | 10/1981 | Pocius ......................... 162/161 |
| 4,297,224 A | 10/1981 | Macchiarolo et al. ....... 210/755 |
| 4,324,635 A | 4/1982 | Sweeney .................... 204/266 |
| 4,325,934 A | 4/1982 | Swindells et al. ........... 423/478 |
| 4,330,531 A | 5/1982 | Alliger ........................ 424/149 |
| 4,370,305 A | 1/1983 | Affonso ....................... 422/292 |
| 4,376,787 A | 3/1983 | Lentsch et al. ............. 424/315 |
| 4,460,373 A | 7/1984 | Beavan ........................... 8/103 |
| 4,542,008 A | 9/1985 | Capuano et al. ............ 423/477 |
| 4,547,381 A | 10/1985 | Mason et al. ................ 426/316 |
| 4,585,482 A | 4/1986 | Tice et al. ................ 106/15.05 |
| 4,689,169 A | 8/1987 | Mason et al. ........... 252/186.24 |
| 4,832,972 A | 5/1989 | Toledo-Flores et al. ..... 423/327 |
| 4,878,361 A | 11/1989 | Kohl et al. .................... 62/352 |
| 4,907,422 A | 3/1990 | Kohl et al. .................... 62/352 |
| 4,908,188 A | 3/1990 | Jefferis, III et al. ........ 422/111 |
| 4,935,153 A | 6/1990 | Favstritsky et al. ......... 210/755 |
| 4,966,716 A | 10/1990 | Favstritsky et al. ......... 210/775 |
| 4,966,775 A | 10/1990 | Donofrio et al. ............ 424/661 |
| 5,006,264 A * | 4/1991 | Acuna ........................ 210/741 |
| 5,014,523 A | 5/1991 | Kohl ............................ 62/347 |
| 5,091,107 A | 2/1992 | Hutchings .............. 252/187.21 |
| 5,140,831 A | 8/1992 | Kohl et al. .................... 62/347 |
| 5,193,357 A | 3/1993 | Kohl et al. .................... 62/347 |
| 5,208,057 A | 5/1993 | Greenley et al. ............ 426/332 |
| 5,229,072 A | 7/1993 | Tarancon ...................... 422/37 |
| 5,289,691 A | 3/1994 | Schlosser et al. .............. 62/78 |
| 5,360,609 A | 11/1994 | Wellinghoff ............. 514/772.3 |
| 5,382,520 A | 1/1995 | Jenson et al. ................. 436/55 |

(Continued)

OTHER PUBLICATIONS

U.S. Appl. No. 10/194,184, filed Jul. 12, 2002, Kilawee et al.

*Primary Examiner*—Gladys JP Corcoran
*Assistant Examiner*—Sean E. Conley
(74) *Attorney, Agent, or Firm*—Kinney & Lange, P.A.

(57) ABSTRACT

A device and method for sanitizing and deodorizing including the selective transportation of a sanitizing composition by the capillary action of a wick to an acidic composition which may be held in a reservoir, or which also may be selectively transported through the capillary action of a wick to the reservoir.

14 Claims, 3 Drawing Sheets

U.S. PATENT DOCUMENTS

| | | |
|---|---|---|
| 5,408,834 A | 4/1995 | Schlosser et al. ............... 62/78 |
| 5,458,851 A | 10/1995 | Schroeder et al. ............. 422/28 |
| 5,476,579 A | 12/1995 | Choi et al. ..................... 204/95 |
| 5,586,439 A | 12/1996 | Schlosser et al. ............... 62/78 |
| 5,631,300 A | 5/1997 | Wellinghoff ............. 514/772.3 |
| 5,639,295 A | 6/1997 | Wellinghoff et al. ..... 106/15.05 |
| 5,639,559 A | 6/1997 | Mason et al. ............... 423/472 |
| 5,650,446 A | 7/1997 | Wellinghoff et al. ..... 514/772.3 |
| 5,695,814 A | 12/1997 | Wellinghoff et al. ........ 427/213 |
| 5,705,050 A | 1/1998 | Sampson et al. ........... 205/687 |
| 5,705,092 A | 1/1998 | Wellinghoff et al. ... 252/187.21 |
| 5,707,739 A | 1/1998 | Wellinghoff et al. ........ 428/403 |
| 5,752,393 A | 5/1998 | Schlosser et al. ............. 62/303 |
| 5,787,723 A | 8/1998 | Mueller et al. ............... 62/347 |
| 5,788,687 A | 8/1998 | Batich et al. ........... 604/890.1 |
| 5,853,689 A | 12/1998 | Klatte ........................ 423/478 |
| 5,871,153 A * | 2/1999 | Doggett, Jr. ................. 239/34 |
| 5,878,583 A | 3/1999 | Schlosser et al. ............... 62/73 |
| 5,888,528 A | 3/1999 | Wellinghoff et al. ........ 424/405 |
| 5,914,120 A | 6/1999 | Wellinghoff et al. ........ 424/406 |
| 5,922,776 A | 7/1999 | Wellinghoff et al. ...... 514/772.3 |
| 5,953,925 A | 9/1999 | Mueller et al. ................. 62/73 |
| 5,965,264 A | 10/1999 | Barenberg et al. .......... 428/402 |
| 5,967,202 A | 10/1999 | Mullen et al. ............... 141/104 |
| 5,974,810 A | 11/1999 | Speronello ..................... 62/66 |
| 5,980,826 A | 11/1999 | Barenberg et al. ............ 422/37 |
| 5,984,993 A | 11/1999 | Mainz et al. .................. 71/12 |
| 6,004,439 A | 12/1999 | Bakhir et al. ............... 204/260 |
| 6,046,243 A | 4/2000 | Wellinghoff et al. ..... 514/772.3 |
| 6,071,483 A | 6/2000 | Pastore ....................... 422/255 |
| 6,071,539 A | 6/2000 | Robinson et al. ........... 424/466 |
| 6,077,495 A | 6/2000 | Speronello et al. ......... 423/477 |
| 6,134,907 A | 10/2000 | Mueller et al. ............... 62/351 |
| 6,171,558 B1 | 1/2001 | Simpson .................. 422/186.3 |
| 6,196,007 B1 | 3/2001 | Schlosser et al. ............... 62/73 |
| 6,238,643 B1 | 5/2001 | Thangaraj et al. .......... 423/477 |
| 6,324,863 B1 * | 12/2001 | Henry ........................ 62/347 |
| 6,764,661 B1 * | 7/2004 | Girard ........................ 422/305 |
| 2002/0148036 A1 * | 10/2002 | Wilson et al. .................. 4/231 |

* cited by examiner

DEODORIZING AND SANITIZING EMPLOYING A WICKING DEVICE

FIELD OF THE INVENTION

The present invention relates to a method and device employing a wicking system which allows continuous and controlled sanitization and deodorization.

BACKGROUND OF THE INVENTION

Chlorine dioxide has been found to be an especially effective disinfectant. As used herein, the term "disinfecting" shall be used to include sanitizing, deodorizing, sterilizing, or otherwise destroying or reducing germ populations. The term "germs" as used herein shall include bacteria, yeasts, molds, viruses or any micro-organism whose presence, and numbers, are deemed inimical to human or animal welfare. Its use has been found to be particularly advantageous where microbes and/or organic odorants are sought to be controlled on and around foodstuffs, as chlorine dioxide functions without the formation of undesirable side products such as chloramines or chlorinated organic compounds that can be produced when elemental chlorine is utilized for the same or similar purposes.

Additionally, at concentrations which have been found to be effective for deodorization and for most antimicrobial applications, chlorine dioxide gas is also generally considered as safe for human contact because the concentrations required are so low.

Certain difficulties are encountered with the use of chlorine dioxide in practice, however. Chlorine dioxide gas can be toxic to humans at concentrations greater than 1,000 ppm and it can be explosive at concentrations above about 0.1 atmosphere. Therefore, chlorine dioxide gas is not manufactured and shipped under pressure like other industrial gases, and conventional methods of on-site manufacture require not only expensive generation equipment but also high levels of operator skill to avoid generating dangerously high concentrations. These problems have substantially limited the use of chlorine dioxide to large commercial applications, such as water treatment and poultry processing, where the consumption of chlorine dioxide is sufficiently large that it can justify the capital and operating costs of expensive equipment and skilled operators for on-site manufacture. However, it is not practical to ship chlorine dioxide as a concentrated gas to the medium or small users.

It has thus become common practice to employ a chlorine dioxide-liberating compound such as sodium chlorite powder which is much safer from the standpoints of storage, shipping and handling. Generation of the chlorine dioxide from sodium chlorite or other chlorine dioxide liberating compound is usually effected by addition of acid, bleach (hypochlorite), or chlorine to the chlorine dioxide liberating compound.

However, the composition obtained from the interaction of the relatively high concentrations of sodium chlorite and acid materials used can be injurious to health. Significantly, the toxicity problem imposes severe limitations on the general utility of the disinfectant composition, particularly with respect to the treatment of human beings.

Methods have been developed in an attempt to overcome the aforementioned problems, but improved methods of generating chlorine dioxide on a small scale are still desired.

SUMMARY OF THE INVENTION

The present invention relates to methods and devices for providing a sanitizing gas, a sanitizing liquid, or both, to locations which are difficult to reach, in particular drains for water flow systems which can plug with mildew and mold, and head spaces for beverage machines and automatic ice making units, for example, which have areas which are difficult to clean and sanitize using standard methods. The methods and devices of the present invention find utility for providing a continuous and controlled treatment of such locations.

In one aspect, the present invention relates to. devices and methods for providing a sanitizing gas, a sanitizing liquid, or both, by reacting a first liquid chemical component and a second liquid chemical component in a reservoir to produce a gaseous sanitizing/deodorizing composition, a liquid sanitizing/deodorizing composition, or both. The device includes at least a first container for the first liquid chemical component and at least on reservoir wherein the liquid components are brought into contact. The first liquid chemical component is provided to the reservoir through the use of a wick or other capillary means. The second liquid chemical component may be provided in the reservoir, or may also be provided to the reservoir from a second container through the use of a wick or other capillary means.

This device is particularly suitable for the production of chlorine dioxide wherein the acidic component is provided in excess either in the reservoir, or by wicking through the use of a wick which is larger than that employed for wicking of a metal chlorite composition.

In another aspect, the present invention relates to methods and devices for the production of controlled quantities of chlorine dioxide at concentrations which are effective to function as a deodorant or a germicide. Aqueous chlorite compositions such as aqueous sodium chlorite are brought into contact at a controlled rate through capillary means, e.g. a wick or a capillary tube, with an acidic liquid composition which will react with the chlorite and form chlorine dioxide.

The acidic liquid composition may either be kept stationary in a reservoir wherein the aqueous chlorite composition is "dripped" into the acidic liquid composition through the use of a wick or capillary tube, for example, or the acidic liquid composition may also be transported by capillary action to the common reservoir wherein the acidic liquid composition and the metal chlorite composition can start reacting.

The reacting mixture may produce a gas which may be released into an enclosure such as an ice machine head space for deodorizing and sanitizing, and may also produce a liquid sanitizing and deodorizing composition which may be released into the drain of a water flow system such as an ice bin drain and/or a floor drain for the automatic ice making unit.

Other systems which employ the use of a drain include wet bars, beverage machines, and so forth.

The reacting mixture may be brought into contact with a drain through the use of gravitational forces through an overflow outlet, by siphoning, by dripping through a small outlet port or tube, and so forth.

In another aspect, the present invention relates to a sanitizing and/or deodorizing system including a first container for holding a first liquid composition including at least one acidic compound, a second container for holding a second liquid composition including at least one compound capable of reacting with the acidic compound to form a sanitizing compound, and a reservoir equipped with an outlet port and/or vent. The first container further has a first conduit extending from the first container to the reservoir with a wick disposed in the conduit for transporting the first liquid to the reservoir. The second container further has a second conduit extending from the second container to the reservoir with a second wick disposed in the second conduit for transporting the second liquid to the reservoir.

Alternatively, the second liquid may be provided in the reservoir in molar excess to the first liquid and the first liquid provided to the reservoir from the first container to the reservoir by the capillary action of a wick.

From the reservoir, the liquid sanitizing mixture may be allowed to exit via an overflow outlet in the reservoir by gravitational forces through a conduit and to the location which is selected for treatment.

The reservoir may also be vented or otherwise open to the atmosphere above it where it may be used to deodorize/sanitize enclosed spaces.

In one embodiment of this invention, the device is employed to continuously treat a drain with a sanitizing composition to prevent a build-up of mold or mildew which may result in a clogged drain.

In one embodiment, the device is employed to continuously provide controlled amounts of gas to the head space of an automatic ice making unit.

The present invention finds particular utility for treating areas which are otherwise difficult to access. The present invention finds particular utility for the treatment of drains for water flow systems wherein mold and mildew may build up causing clogging of the drains.

Furthermore, the present invention is particularly advantageous for treating smaller, enclosed spaces because a gaseous deodorizing/sanitizing composition may be produced in some embodiments. For example, small amounts of chlorine dioxide gas may be generated over a sustained period of time in amounts as low as about 0.5 to about 1.5 ppm. For some applications it is desirable to generate amounts as low as about 0.1 to about 0.5 ppm and more suitably about 0.1 to about 0.3 ppm. The latter range is particularly advantageous for treating the head space above the sump in an automatic ice making machine.

Other sanitizing compositions include quaternary ammonium compounds and peracetic acid, for example.

In another aspect, the present invention relates to a method of treating a drain for a device having a water flow system including the step of selectively transporting a liquid deliming and sanitizing composition from a reservoir to the drain by the capillary action of a wick, by dripping, or by siphoning of said liquid composition.

The liquid deliming and/or sanitizing composition may be provided to the reservoir by the capillary action of a wick from a first container and/or second container. The deliming composition may be acidic and the sanitizing composition may include a metal chlorite.

In another aspect, the present invention relates to a method of treating the head space in equipment having an automatic water circulation system including the steps of providing an acidic aqueous composition in a reservoir and selectively transporting an aqueous metal chlorite composition to the acidic aqueous composition by capillary action of a wick or other capillary means. Chlorine dioxide gas is emitted to said head space.

The device and method of the present invention may be employed in combination with the device and method as described in commonly assigned copending U.S. pat. No. 6619051/DUAL CLEANING AND SANITIZING SYSTEM incorporated by reference herein in its entirety.

Other variations and modifications of the present invention will become apparent to those of ordinary skill in the art by the following embodiments described in detail below.

DETAILED DESCRIPTIONS OF THE PREFERRED EMBODIMENTS

While this invention may be embodied in many different forms, there are described in detail herein specific embodiments of the invention. This description and the drawings described herein, are an exemplification of the principles of the invention and are not intended to limit the invention to the particular embodiments illustrated. Variations and modifications will become readily apparent to those of skill in the art and are intended to be encompassed within the scope of this invention.

Figure 1:
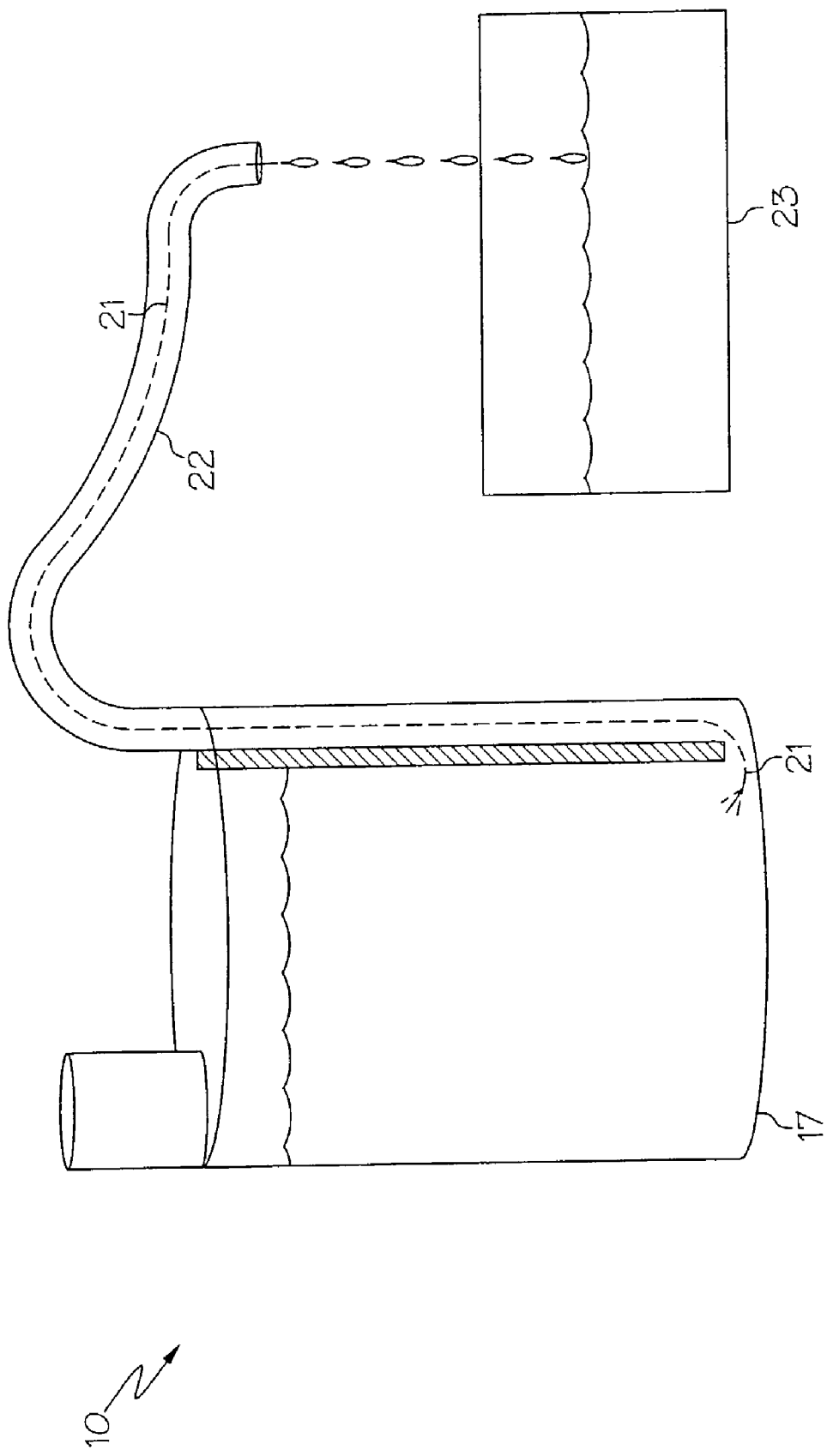
FIG. 1 is a perspective view of a one-wick embodiment of the device according to the present invention.

Turning now to the figures, FIG. 1 shows a generally at 10 one embodiment of the device of the present invention. In this embodiment, chamber 17 is sized such that it contains 8 oz. of an aqueous composition of sodium chlorite at a concentration of about 6%. TYGON® tubing (¼ inch) 22 is attached to the container 10, and may actually be molded into the container 10. A wick 21 is fed through the TYGON® tubing and into the aqueous chlorite composition. The wick size may be varied to control the rate of wicking of sodium chlorite composition. For example, a string weighing 0.13 g per foot may be employed to achieve a rate of about 1 drop per every 15 minutes. In this particular embodiment, the quantity of product delivered is such that the reactants will have a 30 day life expectancy until replenishment is required.

The type of wick employed may be any standard cotton string or candle wick, for example. The candle wicks suitable may range in wick size from about 0.1 g/foot to about 0.5 g/foot including sizes of about 0.3 g/foot and about 0.4 g/foot.

A device similar to the one described above is found in U.S. Pat. No. 3,334,789 the entire content of which is incorporated by reference herein.

Figure 2:
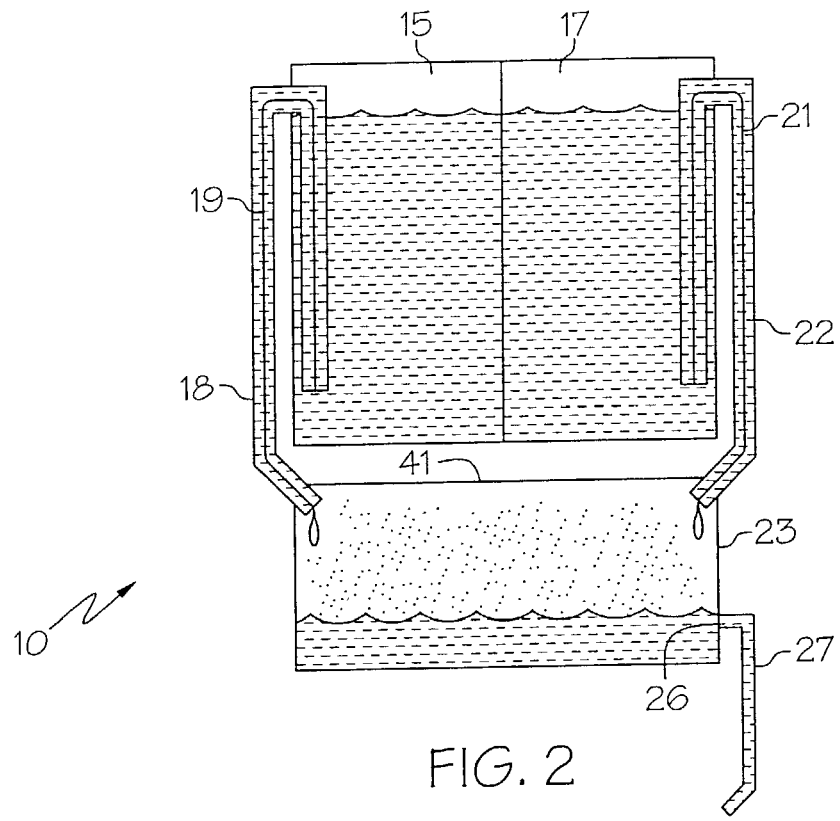
FIG. 2 is a side view of an ice machine incorporating the device in one embodiment according to the present invention.

FIG. 2 illustrates generally at 10 a two-wick embodiment of the device according to the present invention. Device 10 has a first chamber 15 for containing an acid source in liquid form and a second chamber 17 for containing a chlorite source in liquid form. Each chamber 15, 17 is equipped with a conduit 18, 22 which each has a wick 19, 21 respectively. Each wick 19, 21 is fed into a reservoir 23 where the acid and chlorite are mixed forming chlorine dioxide. The reservoir 23 is equipped with an outlet 26 and an overflow tube 27. Once the level of the sanitizing mixture is at or above the level of the outlet 26 then the sanitizing liquid will drain from the reservoir 23 through overflow tube 27 to the desired location such as drain water for a water flow system. This device may be employed for treating any type of area which is capable of draining, and which is conducive for antimicrobial growth such as mold and fungus.

In the embodiment described above, the first chamber 15 may contain an acidic deliming composition such as LIME-A-WAY® available from Ecolab, Inc. in St. Paul, MN, and the second chamber 17 may contain an aqueous sodium chlorite sanitizing composition. LIME-A-WAY® is a phosphoric acid based delimer available from Ecolab, Inc. in St. Paul, MN. Phosphoric acid is suitable for use because it not hazardous for contact with food. Other examples of useful delimers include, but are not limited to: sulfuric acid, hydrochloric acid, citric acid, and so forth.

An excess amount of acid may be transported from first chamber 15 to reservoir 23 by the capillary action of a wick 19 along with the sodium chlorite from second chamber 17 to reservoir 23 by the capillary action of a wick 21. Wick 19 is desirably larger than wick 21 in order to provide an excess amount of acid over sodium chlorite. A reaction begins in reservoir 23 between the sodium chlorite and the acid wherein chlorine dioxide in both a gaseous and a liquid state, is produced. This reaction may be represented by the following general formula:

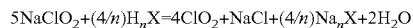

$$5NaClO_2 + (4/n)H_nX = 4ClO_2 + NaCl + (4/n)Na_nX + 2H_2O$$

Figure 3:
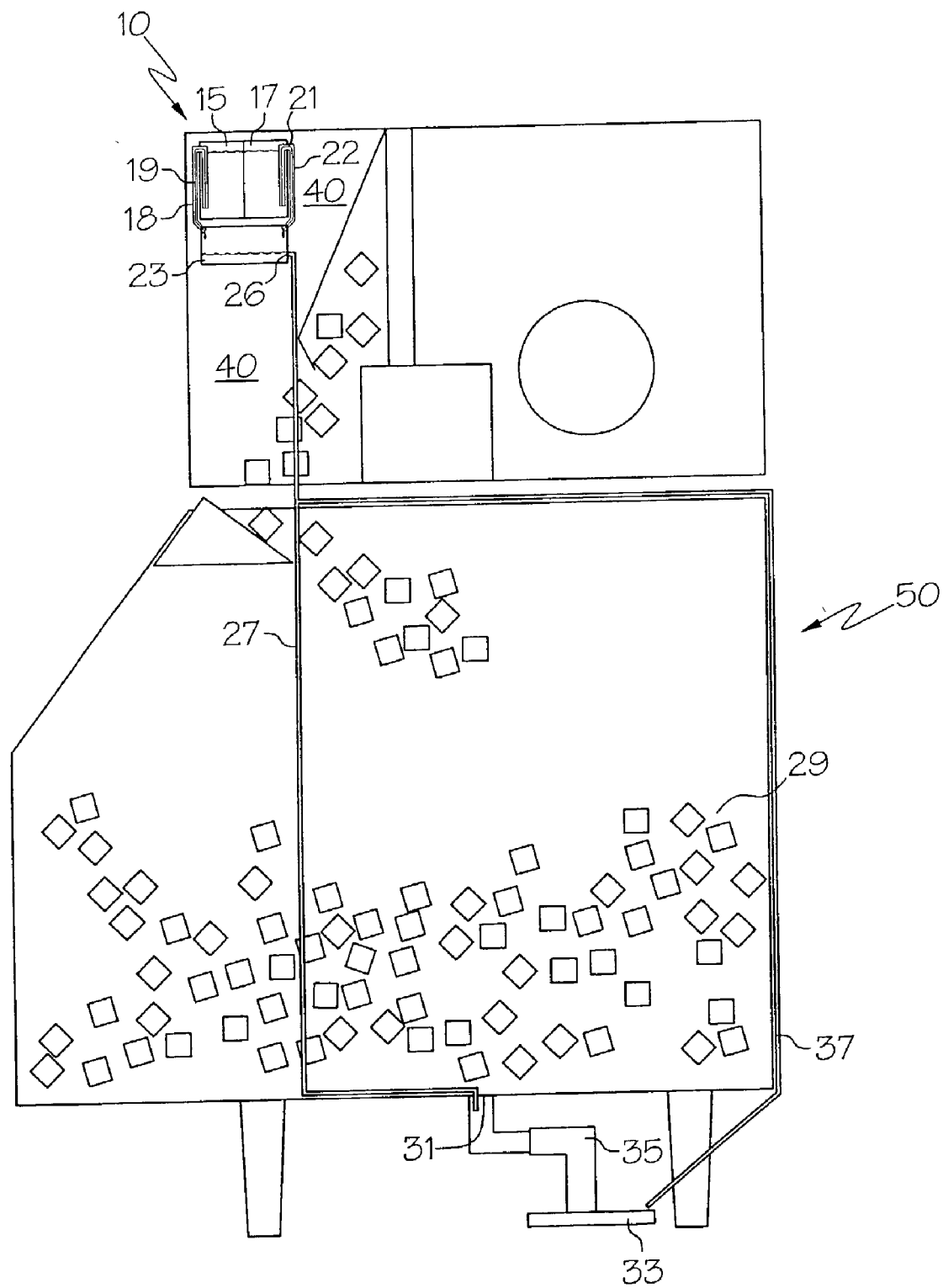
FIG. 3 is a front view of a two-wick embodiment of the device according to the present invention.

Once the level of the acid/sodium chlorite mixture has reached an overflow level above outlet 26, the aqueous chlorine dioxide containing composition may then exit through outlet 26 and proceed by gravitational forces through overflow tube 27 to drain 31 shown in FIG. 3. Alternatively, the aqueous composition may be siphoned, may be dripped through a small outlet in the bottom of the reservoir, or may also be transported by the capillary action of a wick from reservoir 23 to a drain (shown in FIG. 3, below), for example.

Chlorine dioxide gas may also escape through the top 41 of reservoir 23. Alternatively, a vent (not shown) may be provided in the top 41 of the reservoir 23. In this fashion, chlorine dioxide gas may be used as an antimicrobial agent to treat the head space of an enclosed area such as in a beverage machine, ice machine, or the like. This is particularly advantageous for treating areas, such as corners, or behind equipment parts, which are otherwise difficult to access for cleaning.

Chlorine dioxide is particularly suitable for use herein because it partitions itself in both the gas phase and the liquid phase. Chlorine dioxide partitions at a ratio of about 5 ppmv (partial volume) in air and about 1 mg/liter in water under cold water conditions. This partitioning effect allows for sanitization of areas that are difficult to reach with a liquid, i.e. the non-wetted areas. For example, in high humidity and temperature, mold, yeast, fungi, and other microbes may build in head space areas of equipment, such as ice machines, where it is difficult to access for cleaning purposes. Such partitioning makes chlorine dioxide particularly suitable to sanitize the head space of an ice machine, for instance.

However, this is not to say that other sanitizers may not be employed in a liquid state for treatment of drains, for example. Such other useful sanitizers include, but are not limited to: a quaternary ammonium composition, a peracetic acid composition, and so forth.

The entire device 10 may be manufactured such that it is disposable when the reactants have been depleted. Alternatively, chambers 15, 17 may be removable such that they can be easily restocked, for example, or each chamber may simply be replenished with acid and/or sanitizer. As an excess of acid is required, it may be desirable to provide a larger chamber 15.

The above device may be optionally equipped with a battery operated alarm, or LED, which is capable of indicating when one and/or both reactants have been depleted.

In another embodiment as shown in FIG. 3, a two-wick embodiment of the device 10 as shown in an enlarged form in FIG. 2, is shown in combination with an ice machine 50 wherein device 10 is employed to treat both the ice bin drain 31 and the floor drain 33. Device 10 is shown with dual chambers 15, 17 wherein chamber 15 may contain an acid source in the form of a liquid, for example, and chamber 17 may contain a chlorite source in the form of a liquid. A wick 19 inside a conduit 18 is in contact with the acid source in chamber 15 and a wick 21 inside a conduit 22 is in contact with the chlorite source in chamber 17. Conduits 18, 22 may be formed from a flexible polymeric material, for example, such as a Tygon® tubing. Both wicks 19, 21 are configured and arranged such that they will transport a steady supply of acid and chlorite to reservoir 23 which is equipped with an outlet 26 and overflow tube 27 which continues through the ice machine 50 and down to the ice bin drain 31 from which it drains into the floor drain 33 via a plumbing conduit 35. Alternatively, the ice drain 31 may be arranged directly over the floor drain 33 such that little or no plumbing conduit is required.

Alternatively, overflow tube 27 may be equipped with an additional branch conduit 37 which drains directly into the floor drain 33, as shown. Overflow tube 27 may be used alone or in combination with branch conduit 37.

As an excess of acid is desirable, the wick 19 employed for transporting the acid to the reservoir 23 is desirably of a larger grade than the wick 21 employed for transporting the chlorite source to the reservoir 23.

Additionally, reservoir 23 may be configured such that it is open to the head space 40 of the ice machine 50 as shown in this embodiment allowing chlorine dioxide gas to escape and treat areas in the head space 40, such as the corners, which are typically difficult to reach using standard cleaning methods. The head space 40 is also conducive for formation of microbial growth such as molds and fungus due to the presence of moisture, and it is also warmer than other parts of the ice machine 50.

The ice bin drain 31 could be arranged such that it is directly over the floor drain 33 or it may be connected to the floor drain 33 via a plumbing conduit 35 as shown in this embodiment. In this manner, both the ice bin drain 31 and the floor drain 33 are treated with chlorine dioxide. This will help to prevent clogging of the drains 31,33 by the build up of mold and fungus in those areas. Mold and fungus tend to propagate in moist areas such as drains for water flow systems.

While in this embodiment, the device is shown in combination with an ice machine, the invention certainly may find utility to treat drains for any water flow system.

Figure 4:
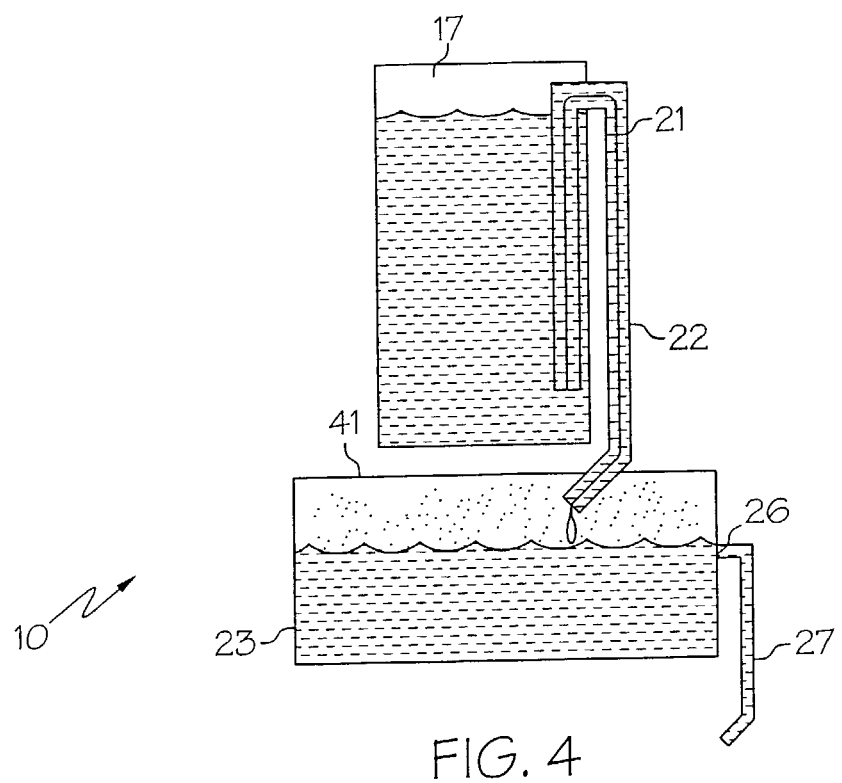
FIG. 4 is a front view of a one-wick embodiment of the device according to the present invention.

FIG. 4 shows generally at 10, an alternative one-wick embodiment according to the present invention. In this embodiment, device 10 has only one chamber 17 for containing a chlorite source. Chamber 17 is equipped with a conduit 22 containing a wick 21. Device 10 also has a reservoir 23 but in this instance reservoir 23 contains the acid source. Wick 21 transports the liquid having chlorite ions from chamber 17 to reservoir 23 wherein the acid and the chlorite ions react to form chlorine dioxide. Reservoir 23 is further equipped with an overflow conduit 27. The overflow conduit 27 and the reservoir 23 are in fluid communication via outlet 26. When the level of liquid sanitizer in reservoir 23 reaches a level above outlet 26, then the liquid drains through overflow conduit 27 to the desired location such as a drain for a water flow system.

The device of the present invention may be advantageously used in combination with other treatment systems for water flow systems such as those described in copending attorney docket number E14.2-9863, in U.S. Pat. No. 5,752,393, and in U.S. Pat. No. 5,289,691, for example, each of which is incorporated by reference herein in its entirety. The present invention is useful for treating areas where a build-up of mold and mildew may occur such as moist areas. Such build-up may be compounded if the area is also warm.

The present invention is particularly advantageous for treating drains for water flow systems.

The device of the present invention may also find utility for deodorizing in small areas such as athletic lockers, food storage containers, walk-in freezers, storage closets such as those for cleaning products, and so forth. In such applications where only deodorizing is required, no outlet 26 or overflow tube 27 are required.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The following non-limiting examples further illustrate the present invention.

EXAMPLES

Example 1

A device similar to that shown in FIG. 1 with an 8 oz. bottle is filled with an acidic delimer composition, LIME-A-WAY, a phosphoric acid based delimer available from Ecolab, Inc. in St. Paul, Minn. Standard cotton string having a weight of 0.13 g/foot was employed. The string was double in order to provide a dosing based on 8 oz/30 days or 0.2667 oz/day (7.89 ml/day). The rate is equal to about 1 drop from the wick every 15 minutes. The wick was contained in ¼" TYGON® tubing.

The bottle was placed on a balance and monitored over time. The following data was collected.

TABLE 1

| Time | Weight loss | g/minute |
|---|---|---|
| 43 min | 1.41 g | 0.033 g/min |
| 56 min | 1.33 g | 0.033 g/min |
| 18 hrs 5 min | 26.27 g | 0.024 g/min |
| 18 hrs 15 min | 26.54 g | 0.024 g/min |
| 19 hrs 40 min | 28.28 g | 0.024 g/min |
| 19 hrs 59 min | 28.72 g | 0.024 g/min |
| 21 hrs 15 min | 30.28 g | — |
| 23 hrs 22 min | 32.89 g | — |
| 25 hrs 6 min | 34.97 g | — |
| 42 hrs 39 min | 53.21 g | — |

Example 2

The same procedure was followed as in Example 1 with the exception that the 0.13 g/foot cotton string was not doubled in this experiment. The data found in the following Table 2 was collected. The device was found to provide about 0.05 oz/day.

It was noted that as the level of product drops in the chamber, the distance that the product needs to travel up the wick is farther and it appears to slow down the rate of dispensing.

TABLE 2

| Time | Weight loss | g/minute (avg wt loss) |
|---|---|---|
| 17 hrs 12 min | 2.24 g | |
| 18 hrs 46 min | 2.41 g | |
| 20 hrs 21 min | 2.58 g | 0.0022 g/min |
| 22 hrs 28 min | 2.72 g | 0.0021 g/min |
| 24 hrs 12 min | 2.92 g | 0.0021 g/min |
| 41 hrs 45 min | 3.83 g | 0.0020 g/min |
| 43 hrs 11 min | 3.93 g | 0.0020 g/min |
| 44 hrs 7 min | 4.04 g | — |
| 46 hrs 29 min | 4.21 g | — |
| 48 hrs 32 min | 4.39 g | — |
| 112 hrs 31 min | 9.11 g | — |
| 136 hrs 46 min | 10.01 g | — |
| 143 hrs 45 min | 10.31 g | — |
| 160 hrs 48 min | 10.97 g | — |
| 184 hrs 38 min | 11.28 g | — |

Example 3

A device according to the present invention was tested in Manitowoc Automatic Ice Making Unit. A wick feed available from Clack Corp. using a medium size candle wick of 0.313 g/foot was filled with a sodium chlorite composition at a concentration of about 6% sodium chlorite. This dispenser was found to dispense about 0.40-0.50 oz/day according to the following data.

The dispenser was installed on the top of a Manitowoc Automatic Ice Making Unit and the feed tube was fed through a hole into a 400 ml disposable beaker which was mounted on the inside wall of the ice machine. The beaker contained 50 g of LIME-A-WAY®. The liquid chlorite solution was dripped into the 400 ml beaker. The amount of chlorine dioxide was then monitored in the head space of the ice machine. The following results were obtained.

TABLE 3

| Time | Chlorine Dioxide in air (ppm) |
|---|---|
| 8:00 am | 0.01 |
| 9:40 am | 0.55 |
| 11:00 am | 0.87 |
| 11:45 am | 0.38 |
| 1:05 pm | 0.67 |
| 2:20 pm | 0.61 |

The acid/chlorite mixture was also analyzed for chlorine dioxide in solution by diluting 25 ml at a ratio of 10:1. The concentration of chlorine dioxide was found to be 0.79 ppm and the original solution thus had 7.9 ppm chlorine dioxide.

The same test was repeated and continued for a longer period of time with the following results.

TABLE 4

| Day | Time | Chlorine Dioxide in air (ppm) |
|---|---|---|
| Day 1 | 7:00 am | 0 |
| | 8:00 am | 0.07 |
| | 9:20 am | 0.47 |
| | 10:40 am | 1.23 |
| | 11:30 am | |

TABLE 4-continued

| Day | Time | Chlorine Dioxide in air (ppm) |
|---|---|---|
| | 12:20 pm | |
| | 2:50 pm | |
| Day 2 | 6:30 am | 0.74 |
| | 8:00 am | 0.85 |
| | 10:00 am | 0.78 |
| | 12:30 pm | 0.63 |
| Day 3 | 6:30 am | 0.65 |
| | 10:00 am | 0.67 |
| Day 4 | 7:30 am | 1.05 |
| Day 5 | 7:30 am | 0.39 |
| Day 6 | 8:10 am | 0.42 |
| | | 0.64 |
| Day 7 | 6:30 am | 0.43 |

The amount of sodium chlorite contained in the Clack Dispenser was dropped to the "low level" line between Day 4 and Day 5 to determine if the delivery rate dropped significantly. As can be seen from the data, the rate did drop off some, but was still acceptable.

The invention claimed is:

1. A sanitizing system for use in an automatic water flow system with at least one drain comprising:
   a) a first container for holding a first liquid composition comprising at least one acidic compound;
   b) a second container for holding a second liquid composition comprising at least one compound capable of reacting with said acidic compound to form a sanitizing compound;
   c) a reservoir having a vent and an outlet port, said outlet port in fluid communication with the drain of the automatic water flow system;
   d) a first conduit having an inlet in said first container and an outlet in said reservoir and a first wick disposed in said first conduit and extending from said first container to said reservoir;
   e) a second conduit having an inlet in said second container and an outlet in said reservoir and a second wick disposed in and extending through said second conduit from said second container to said reservoir;
   wherein said first liquid composition and said second liquid composition form a reactive mixture in said reservoir.

2. The sanitizing system of claim 1 wherein said automatic water flow system is in fluid communication with a second drain via a third conduit which is connected to said reservoir at said outlet port, wherein said reactive mixture in said reservoir is transported through said outlet port of said reservoir to said second drain and is transported through said exit port of said second drain and is transported to said second drain by gravity.

3. The sanitizing system of claim 1 wherein said reactive mixture is transported from said reservoir to said drain.

4. The sanitizing system of claim 1 wherein said outlet port is equipped with a valve system.

5. The sanitizing system of claim 1 where said reactive mixture is transported to said at least one drain when a level of said reactive mixture in said reservoir reaches a same level of said outlet port.

6. The sanitizing system of claim 1 wherein said first liquid composition comprises a delimer.

7. The sanitizing system of claim 1 wherein said second liquid composition comprises a metal chlorite.

8. The sanitizing system of claim 1 wherein said at least one drain is an ice bin drain in an automatic ice making unit.

9. The sanitizing system of claim 2 wherein said second drain is a floor drain.

10. The sanitizing system of claim 1 wherein said reactive mixture in said reservoir produces chlorine dioxide in a gaseous state and in a liquid state.

11. The sanitizing system of claim 1 wherein said automatic water flow system is in an automatic ice making unit having a head space.

12. The sanitizing system of claimi 11 wherein said reactive mixture in said reservoir produces chlorine dioxide in a gaseous state and chlorine dioxide in a liquid state and said chlorine dioxide in said liquid state exits said reservoir through said vent into said head space of said automatic ice making unit.

13. The sanitizing system of claim 1 wherein said first liquid composition is in excess to said second liquid composition in said reservoir.

14. The sanitizing system of claim 1 wherein said first wick is larger than said second wick.

* * * * *

UNITED STATES PATENT AND TRADEMARK OFFICE
CERTIFICATE OF CORRECTION

PATENT NO. : 7,285,255 B2 Page 1 of 1
APPLICATION NO. : 10/316513
DATED : October 23, 2007
INVENTOR(S) : Leonard Kadlec et al.

It is certified that error appears in the above-identified patent and that said Letters Patent is hereby corrected as shown below:

Column 10, Line 34, delete "claimi", insert --claim--

Signed and Sealed this

Twenty-fifth Day of March, 2008

JON W. DUDAS
*Director of the United States Patent and Trademark Office*